(12) United States Patent
Kwak et al.

(10) Patent No.: US 10,451,571 B2
(45) Date of Patent: Oct. 22, 2019

(54) MEASURING THE WETTABILITY OF POROUS MEDIA BASED ON THE TEMPERATURE SENSITIVITY OF NUCLEAR MAGNETIC RESONANCE RELAXATION TIME

(71) Applicant: Saudi Arabian Oil Company, Dhahran (SA)

(72) Inventors: Hyung Tae Kwak, Dhahran (SA); Ahmad Mubarak Al-Harbi, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 80 days.

(21) Appl. No.: 15/837,404

(22) Filed: Dec. 11, 2017

(65) Prior Publication Data

US 2019/0178824 A1    Jun. 13, 2019

(51) Int. Cl.
| | | |
|---|---|---|
| *G01N 24/08* | (2006.01) | |
| *G01R 33/50* | (2006.01) | |
| *G01R 33/46* | (2006.01) | |
| *G01V 3/32* | (2006.01) | |

(Continued)

(52) U.S. Cl.
CPC ......... *G01N 24/081* (2013.01); *G01R 33/448* (2013.01); *G01R 33/4625* (2013.01); *G01R 33/4804* (2013.01); *G01R 33/50* (2013.01); *G01V 3/32* (2013.01)

(58) Field of Classification Search
CPC ................ G01R 33/4625; G01R 33/50; G01R 33/4804; G01R 33/448; G01R 33/445; G01N 24/081; G01V 3/32
See application file for complete search history.

(56) References Cited

U.S. PATENT DOCUMENTS

| | | |
|---|---|---|
| 5,162,733 A | 11/1992 | Baldwin |
| 6,765,380 B2 | 7/2004 | Freedman |
| 6,883,702 B2 | 4/2005 | Hurlimann et al. |

(Continued)

OTHER PUBLICATIONS

International Search Report and Written Opinion issued in International Application No. PCT/US2018/062723 dated Mar. 15, 2019, 14 pages.

(Continued)

*Primary Examiner* — Rishi R Patel (74) *Attorney, Agent, or Firm* — Fish & Richardson P.C.

(57) ABSTRACT

The present disclosure describes methods and systems, including computer-implemented methods, computer program products, and computer systems, for measuring wettability of a rock sample. One method includes: at each temperature of a plurality of temperatures, obtaining a first Nuclear Magnetic Resonance (NMR) surface relaxation time for a rock sample having a saturation level; determining a first temperature sensitivity based on the first NMR surface relaxation times and corresponding temperatures; at each temperature of the plurality of temperatures, obtaining a second NMR surface relaxation time for the rock sample that is saturated with oil; determining a second temperature sensitivity based on the second NMR surface relaxation times and corresponding temperature; and determining a wettability of the rock sample based on the first temperature sensitivity and the second temperature sensitivity.

19 Claims, 4 Drawing Sheets

(51) Int. Cl.
   *G01R 33/48*   (2006.01)
   *G01R 33/44*   (2006.01)

(56) References Cited

U.S. PATENT DOCUMENTS

| | | | |
|---|---|---|---|
| 7,397,240 | B2 | 7/2008 | Fleury |
| 9,746,576 | B2 | 8/2017 | Jebutu |
| 2003/0169040 | A1 | 9/2003 | Hurlimann |
| 2006/0132131 | A1 | 6/2006 | Fleury |
| 2012/0241149 | A1 | 9/2012 | Chen |
| 2013/0261979 | A1 | 10/2013 | Al-Muthana et al. |
| 2014/0340082 | A1* | 11/2014 | Yang .................. G01N 24/081 324/309 |
| 2015/0346377 | A1* | 12/2015 | Jebutu .................... G01V 3/32 324/303 |
| 2016/0313267 | A1* | 10/2016 | Kwak .................... G01N 11/00 |

OTHER PUBLICATIONS

Freedman et al., "Wettability saturation, and viscosity from NMR measurements," SPE Jou, Society of Petroleum Engineers, vol. 8, No. 4, Sep. 29, 2003, 11 pages.

Godefroy et al., "Temperature Effect on NMR Surface Relaxation in Rocks for Well Logging Applications," Journal of Physical Chemistry B (106), Oct. 9, 2002, 8 pages.

Kleinberg et al., "Mechanism of NMR Relaxation of Fluids in Rock," Journal of Magnety Resonance, Series A (108), Jun. 1994, 9 pages.

"Temperature dependent $T_2$ spectra in carbonate cores: measurements at ambient pressure," Magritek, Application Note 4, Sep. 2013, 4 pages.

* cited by examiner

MEASURING THE WETTABILITY OF POROUS MEDIA BASED ON THE TEMPERATURE SENSITIVITY OF NUCLEAR MAGNETIC RESONANCE RELAXATION TIME

TECHNICAL FIELD

This disclosure relates to exploration and production of hydrocarbons, and more specifically, to measuring rock wettability using Nuclear Magnetic Resonance (NMR).

BACKGROUND

Rocks in a hydrocarbon reservoir can store hydrocarbons (for example, petroleum, oil, gas, or any combinations thereof) by trapping the hydrocarbons within porous formations in the rocks. Therefore, measurement results of the wettability of the rocks in a reservoir can be used to determine the potential productivity of the reservoir. The wettability can also be used to optimize extraction of the stored hydrocarbons from the reservoir in various steps of a production operation, such as water flooding and enhanced oil recovery (EOR).

SUMMARY

The present disclosure describes methods and systems, including computer-implemented methods, computer program products, and computer systems for measuring rock wettability. One method for measuring wettability of a rock sample includes: at each temperature of a plurality of temperatures, obtaining a first Nuclear Magnetic Resonance (NMR) surface relaxation time for the rock sample having a saturation level; determining a first temperature sensitivity based on the first NMR surface relaxation times and corresponding temperatures; at each temperature of the plurality of temperatures, obtaining a second Nuclear Magnetic Resonance (NMR) surface relaxation time for the rock sample that is saturated with oil; determining a second temperature sensitivity based on the second NMR surface relaxation times and corresponding temperature; and determining the wettability of the rock sample based on the first temperature sensitivity and the second temperature sensitivity.

Other implementations of this aspect include corresponding computer systems, apparatuses, and computer programs recorded on one or more computer storage devices, each configured to perform the actions of the methods. A system of one or more computers can be configured to perform particular operations or actions by virtue of having software, firmware, hardware, or a combination of software, firmware, or hardware installed on the system that, in operation, cause the system to perform the actions. One or more computer programs can be configured to perform particular operations or actions by virtue of including instructions that, when executed by data processing apparatus, cause the apparatus to perform the actions.

The details of one or more implementations of the subject matter of this specification are set forth in the accompanying drawings and the subsequent description. Other features, aspects, and advantages of the subject matter will become apparent from the description, the drawings, and the claims.

DESCRIPTION OF DRAWINGS

Like reference numbers and designations in the various drawings indicate like elements.

DETAILED DESCRIPTION

The following description is presented to enable any person skilled in the art to make and use the disclosed subject matter, and is provided in the context of one or more particular implementations. Various modifications to the disclosed implementations will be readily apparent to those skilled in the art, and the general principles defined in this disclosure may be applied to other implementations and applications without departing from scope of the disclosure. Thus, the present disclosure is not intended to be limited to the described or illustrated implementations, but is to be accorded the widest scope consistent with the principles and features disclosed in this disclosure.

This disclosure generally describes methods and systems, including computer-implemented methods, computer program products, and computer systems, for measuring rock wettability. One technique to understand properties of the hydrocarbon reservoir is to develop computer-generated software models of all, or portions, of the reservoir. To develop such models, a reservoir rock sample from the hydrocarbon reservoir is evaluated and results of the evaluation are provided as an input to the computer software program that generates the software models. The reservoir rock sample can be evaluated by performing one or more of several experiments under laboratory conditions or under reservoir conditions (that is, the conditions experienced by the sample in the hydrocarbon reservoir). Rock wettability, specifically, the wettability of the porous structure within the rock, is one of the parameters of the reservoir rock sample that can be evaluated.

Wetting is the ability of a liquid to maintain contact with a solid surface, which results from intermolecular interactions when two materials are brought together in contact. The wettability, which measures the degree of wetting, is the product of a force balance between adhesive and cohesive forces. Adhesion is the tendency of liquid molecules to create an attraction to a different substance. On the other hand, cohesion causes the liquid drop to create the minimum possible surface area. Hydrophobicity of a solid surface is caused by the adhesive force between liquid and solid. Therefore, wettability of the solid surface is directly related to hydrophobicity. Wettability studies are described in this disclosure in the context of reservoir rock samples, that is, rock samples that can be found in a hydrocarbon reservoir and that can trap hydrocarbons within their pore systems. The studies and the findings described in this disclosure can be applicable to any type of porous media, for example, porous media that include homogeneous pore systems (that is, having pores of substantially same size) or inhomogeneous pore systems (that is, having multiple pore subsystems, each of different sizes).

Wettability can be used as a distinguishing characteristic of reservoir rocks, designating the rocks as either hydrophobic or hydrophilic. Wettability is a material parameter characteristic of a given rock, for example, sandstone, or carbonate, and additionally depends on factors such as surface roughness, surface size, existence of primary adsorption sites, and specific ion effect. Rock wettability is one of the parameters that affect fluid flow through rocks. Rock wettability, therefore, is an input variable for geophysical models that predict flow through reservoir rocks. One technique to determine wettability of a surface (that is, the ability of the surface to retain moisture) is to add a drop of water to a surface and to measure the contact angle of the water on the surface. The determined wettability can be provided as an input variable to geophysical model (a computer-generated or otherwise). The input variable will be more accurate and the predictions of the geophysical models will be more accurate if the wettability were determined for a porous structure of actual rocks, for example, under conditions that resemble and mimic rock environments. In addition, due to the dynamic nature of pore surface wettability during the injecting of various types of fluids, rock wettability at different saturation levels is one of important factors for the prediction of hydrocarbon production. One is the wettability alteration during waterflooding. As more water is introduced into the reservoir, the pore surface becomes more water wet because a large amount of hydrocarbon components attached to the pore surface is being replaced by injected water. Therefore, measuring the wettability at different saturation level is useful in predicting hydrocarbon production.

In some implementations, wettability can be measured based on nuclear magnetic resonance (NMR) surface relaxation times. The NMR surface relaxation time can be defined in the following equation:

$$\frac{1}{T_s} = \rho\left(\frac{S}{V}\right) \qquad (1)$$

where $T_s$ represents the NMR surface relaxation time, $\rho$ represents the surface relaxivity, S represents the total pore surface area, and V represents the total pore volume. NMR surface relaxation times includes T1 surface relaxation times, denoted as $T_{1,s}$ and T2 surface relaxation time, denoted as $T_{2,s}$. $T_{1,s}$ and $T_{2,s}$ can be calculated based on the relaxation time observed in the NMR measures using the following equations:

$$\frac{1}{T_1} = \frac{1}{T_{1,b}} + \frac{1}{T_{1,s}} \qquad (2a)$$

$$\frac{1}{T_2} = \frac{1}{T_{2,b}} + \frac{1}{T_{2,s}} + \frac{1}{T_{2,D}} \qquad (2b)$$

where $T_1$ and $T_2$ represent the T1 and T2 relaxation times that are observed in the during NMR measures, respectively; $T_{1,b}$ and $T_{1,s}$ represent the bulk and the surface relaxation time for T1, respectively; $T_{2,b}$, $T_{2,s}$, and $T_{2,D}$ represent the bulk, the surface, and diffusion relaxation time for T2, respectively. The T1 and T2 relaxation times can also be referred to as T1 and T2 apparent relaxation times, respectively. NMR measurements are sensitive to wettability because of the effect that the solid surface has on promoting magnetic relaxation of the saturating fluid. The magnitude of this effect can depend upon the wettability characteristics of the solid with respect to the liquid in contact with the surface. Therefore, the surface relaxation times $T_{1,s}$ and $T_{2,s}$, are mainly determined by the strength of fluid-rock interaction.

In addition to the fluid-rock interactions, temperature is also a factor on the NMR surface relaxation times. The following equation shows the relationship between temperature and the NMR surface relaxation times:

$$T_{1,2}^a = T_{1,2}^b \exp\left(-\frac{\Delta E}{R}\left(\frac{1}{T_a} - \frac{1}{T_b}\right)\right) \qquad (3)$$

where $T_{1,2}^a$ and $T_{1,2}^b$ denote the T1 and T2 surface relaxation times obtained in temperature $T_a$ and $T_b$, respectively. $\Delta E$ denotes the surface activation energy, which is determined by the properties of the fluid and the pore surface of the rock. R denotes the gas constant, which is 1.99×10−3 Kcal/K mole.

Pore surfaces with different $\Delta E$ values relative to a specific fluid can have different temperature sensitivity of the NMR surface relaxation times. Because for a specific fluid and solid pore surface, $\Delta E$ is fixed. Therefore, the wettability can be measured by temperature sensitivity of the NMR surface relaxation time. If the NMR surface relaxation time is plotted against temperature, the wettability of the surface can be determined from the slope of the plot. For 100% water wet pore surface, the slope is 0 since no oil is relaxing on the surface. On the other hands, for 100% oil wet surface, the slope is a non-zero value that is determined by the $\Delta E$ value. Thus, the wettability of pore surface at a particular water saturation can be quantified by comparing the slopes from a 100% oil saturated sample and a sample saturated with oil at a particular amount of water saturation. This approach provides a non-destructive and non-invasive measurement method for rock samples. FIGS. 1-6 provide additional details of these implementations.

Figure 1:
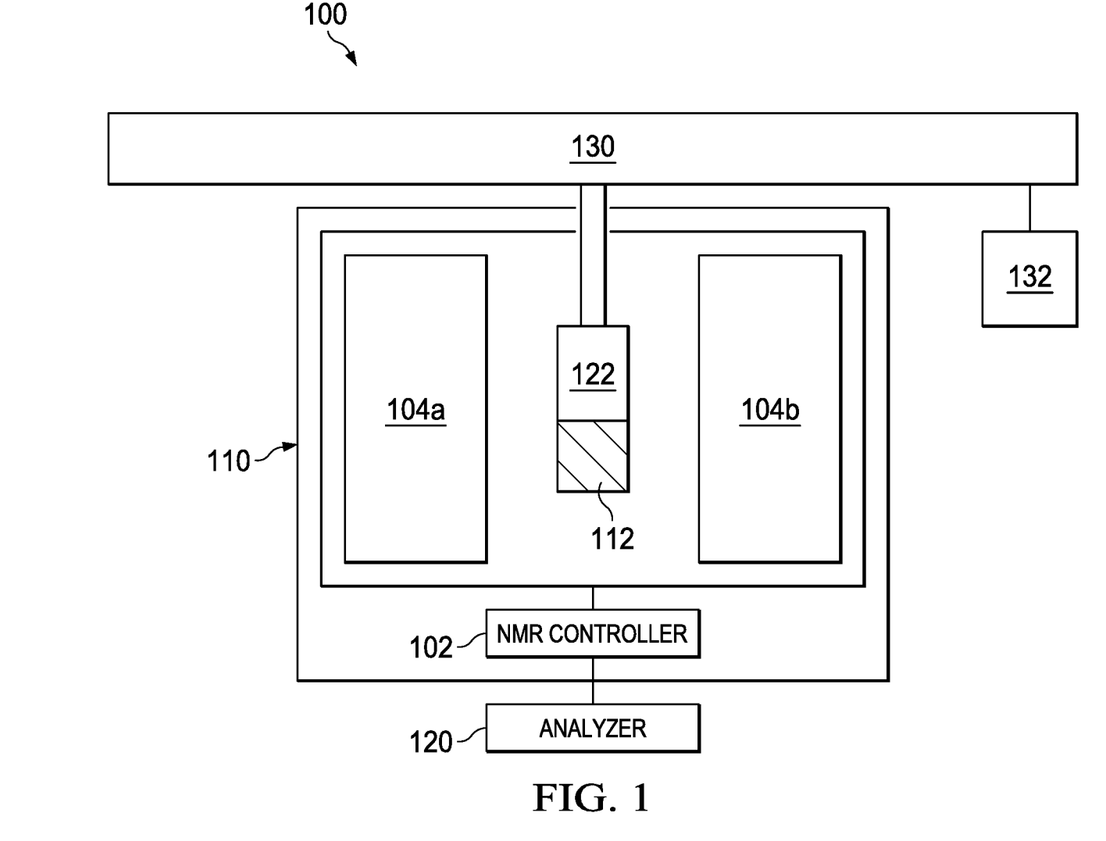
FIG. 1 is a schematic diagram of a system for determining a wettability of a reservoir rock sample based on the Nuclear Magnetic Resonance (NMR) relaxation times, according to an implementation.

FIG. 1 is a schematic diagram of a system 100 for determining a wettability of a reservoir rock sample based on the NMR relaxation times, according to an implementation. The system 100 includes an NMR instrument 110 connected to an analyzer 120 and a water pipe 130. The NMR instrument 110 represents an NMR instrument that is configured to measure NMR relaxation times. Examples of the NMR instrument include a low-field NMR instrument. In some implementations, the NMR instrument 110 can include a NMR controller 102 connected to one or more NMR magnets, for example, a first NMR magnet 104a or a second NMR magnet 104b, or both. In some cases, fluid redistribution during NMR measurements for a range of temperatures may cause the experimental errors, especially for the porous media samples with high permeability. For these types of samples, additional external magnets with high magnetic field can be used to shorten the NMR data acquisition time.

The NMR instrument 110 also includes a NMR sample cell 122. The NMR sample cell 122 is configured to sustain high pressure and high temperature (HPHT) conditions. For example, the NMR sample cell 122 can withstand up to 15,000 pounds per square inch (PSI) and up to 250 degrees Celsius (° C.) for samples of less than 5 millimeter (mm) in diameter or up to 5,000 PSI and up to 150° C. for samples of about 1.5 inch in diameter. A sample 112 is placed in the NMR sample cell 122 for measurement. The sample 112 can be any shape of porous media that can fit the NMR sample cell 122. For example, the sample 112 can be a rock core plug or a rock chip. The NMR controller 102 controls the NMR instrumentation. For example, the NMR controller 102 can provide instructions to the NMR instrumentation to measure the relaxation times at different temperatures. The NMR controller 102 can also receive the measurement results of relaxation times.

The system 100 also includes an analyzer 120. The analyzer 120 can implement computer software operations to determine a wettability of the sample 112 based on the measured relaxation times. In some implementations, the analyzer 120 and the NMR controller 102 can be implemented as different computing devices. Alternatively, the NMR controller 102 and the analyzer 120 can be implemented as a single entity.

The water pipe 130 provides circulating fluid to the NMR sample cell 122. The circulating fluid can be water, oil or other liquids. The water pipe 130 can include other components such as a pump, a gauge, a reservoir that can hold and inject the fluid, or any combinations thereof. The water pipe 130 is connected to a heater 132. The heater 132 can heat the circulating fluid in the water pipe 130. The heater 132 can be set at different temperatures for different NMR measurements.

Figure 2:
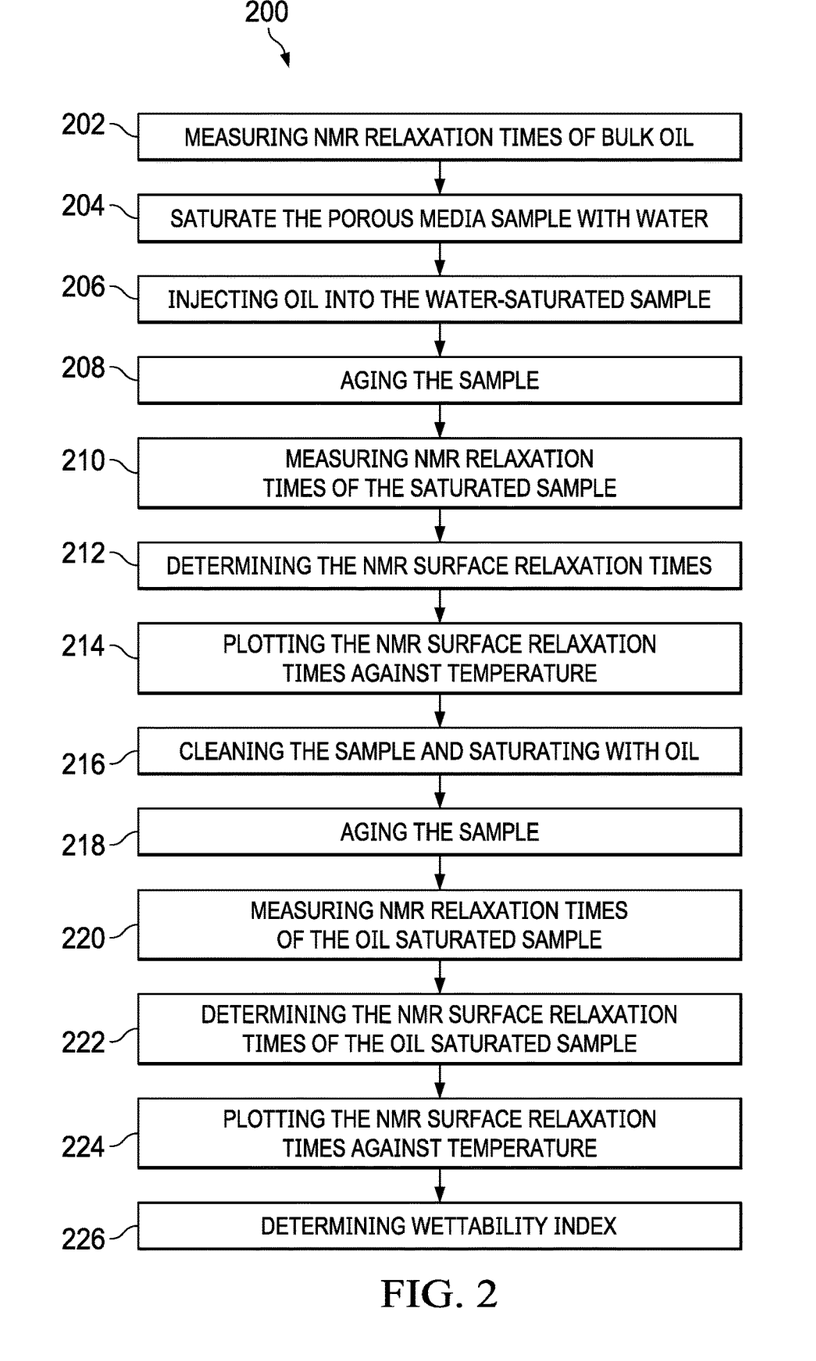
FIG. 2 is an example of a process for measuring wettability of a reservoir rock sample based on NMR surface relaxation times, according to an implementation.

FIG. 2 is an example of a process 200 for measuring wettability of a reservoir rock sample based on NMR surface relaxation times, according to an implementation. For clarity of presentation, the description that follows generally describes process 200 in the context of FIGS. 1 and 3-6. However, it will be understood that process 200 may be performed, for example, by any other suitable system, environment, software, and hardware, or a combination of systems, environments, software, and hardware, as appropriate. In some implementations, various steps of process 200 can be run in parallel, in combination, in loops, or in any order.

At 202, the NMR relaxation times of bulk oil are measured at different temperatures. In some cases, the measured temperature can range between 15 to 85° C. For each temperature, the relaxation times ($T_{1,O,Bulk}$ and $T_{2,O,Bulk}$) of the bulk oil can be recorded. In some implementations, the NMR relaxation times can be obtained using HPHT NMR probes. The temperature of the sample can be controlled by circulating inert fluid, which does not generate an NMR signal. By varying the temperature of the circulating fluid using a heater, the temperatures of measurement can be changed accordingly.

At 204, a porous media sample is saturated with water. The porous media sample can be collected from a reservoir. The porous media sample can be saturated using a core flooding system. In some implementations, heavy water ($D_2O$) is used to saturate the porous media sample. $D_2O$ is chemically equivalent to regular water ($H_2O$) but invisible for hydrogen ($^1H$) NMR signal. Therefore, using heavy water can isolate the NMR signal produced by the oil within the sample.

At 206, the bulk oil that has been measured at 202 is injected into the saturated porous media sample. The bulk oil is injected to create a saturation level S of the porous media sample. The saturation level S is the ratio between the saturated volume of oil and the total pore volume. The saturation level S can take a value between 0 to 100%. The saturation level S can be achieved by controlling the amount of bulk oil injected into the sample and monitoring the saturation level until it reaches the value S. The saturation level can be monitored by using NMR/Magnetic resonance imaging (MRI), or effluent volume analysis through core flooding.

At 208, the injected sample is aged over a time period. The aging process enables the oil to fully bind to the pore surface. In some implementations, the length of the aging time period can be determined based on the NMR relaxation time measurement. The aging time period can terminate if the NMR relaxation times are stabilized. The aging time period can vary for different samples. For example, the aging time period can vary between 2 weeks to 6 weeks. In some cases, the aging time period can be four weeks. In some cases, the sample can be aged by storing in the core flooding cylinder under reservoir temperature and pressure.

At 210, NMR relaxation times of the saturated pore media sample are measured under the same temperatures as step 202. For each temperature, the relaxation times ($T_{1,S,Apparent}$ and $T_{2,S,Apparent}$) of the saturated pore media sample can be recorded.

At 212, for each temperature, the NMR surface relaxation times are calculated based on the bulk oil relaxation times measured at step 202 and the saturated pore media sample relaxation times measured at step 210, using the following equations:

$$\frac{1}{T_{1,s,Surface}} = \frac{1}{T_{1,S,Apparent}} - \frac{1}{T_{1,O,Bulk}} \quad \text{Eq. (2a)}$$

$$\frac{1}{T_{2,s,Surface}} = \frac{1}{T_{2,S,Apparent}} - \frac{1}{T_{2,O,Bulk}} \quad \text{Eq. (2b)}$$

where $T_{1,S,Surface}$ and $T_{2,S,surface}$ represent the calculated T1 and T2 surface relaxation times for a saturation level S.

Figure 3:
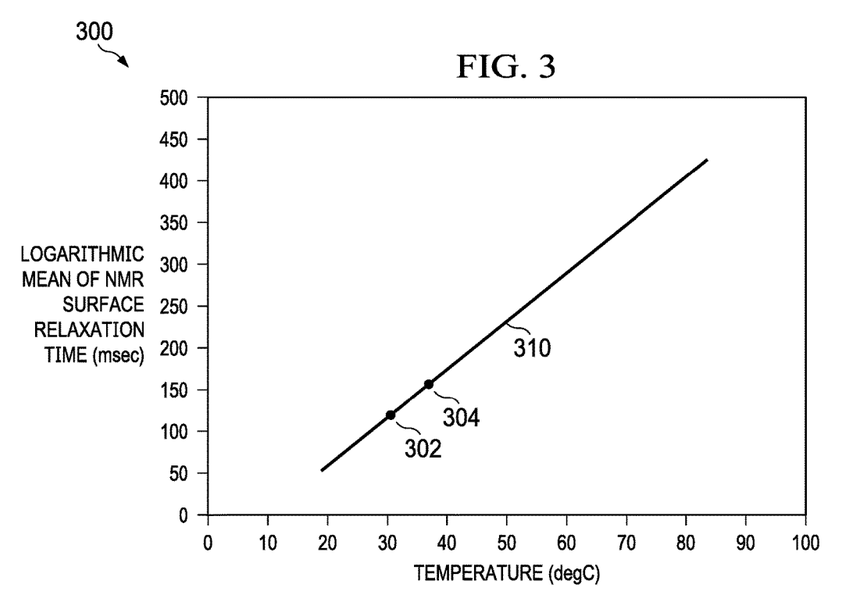
FIG. 3 is a chart illustrating an example plot of the NMR surface relaxation times with temperature, according to an implementation.

At 214, the NMR surface relaxation times can be plotted against the different temperatures. FIG. 3 is a chart 300 illustrating an example plot of the NMR surface relaxation times with temperature, according to an implementation. The data points in chart 300 is obtained in a lab experiment. The x-axis of the chart 300 represents the temperatures under which each measurement is taken, in units of ° C. The y-axis of the chart 300 represents the NMR surface relaxation time calculated at step 212. The y-axis uses a logarithmic scale in units of micro seconds (ms). The points 302 and 304 represent $T_{1,S,Surface}$ for 30 and 40° C., respectively. The line 310 represents the linear relationship of $T_{1,S,Surface}$ and the temperature. A similar line can be obtained based on $T_{2,S,Surface}$ for different temperatures.

At 216, the pore media sample is cleaned and fully saturated with the bulk oil measured at 202.

At 218, the pore media sample saturated with oil is aged over a time period. Similarly to step 208, the length of the aging time period can be determined based on the NMR relaxation time measurement. The aging time period can terminate if the NMR relaxation times are stabilized. The aging time period can vary for different samples. For example, the aging time period can vary between 2 weeks to 6 weeks. In some cases, the aging time period is 4 weeks.

At 220, the NMR relaxation times of the saturated pore media sample are measured under the same temperatures as in step 202. For each temperature, the relaxation times ($T_{1,O,Apparent}$ and $T_{2,O,Apparent}$) of the saturated pore media sample can be recorded.

At 222, for each temperature, the NMR surface relaxation times for the oil saturated sample are calculated based on the bulk oil relaxation times measured at step 202 and the saturated pore media sample relaxation times measured at step 220, using the following equations:

$$\frac{1}{T_{1,O,Surface}} = \frac{1}{T_{1,O,Apparent}} - \frac{1}{T_{1,O,Bulk}} \quad \text{Eq. (2a)}$$

$$\frac{1}{T_{2,O,Surface}} = \frac{1}{T_{2,O,Apparent}} - \frac{1}{T_{2,O,Bulk}} \quad \text{Eq. (2b)}$$

where $T_{1,O,Surface}$ and $T_{2,O,Surface}$ represent the calculated T1 and T2 surface relaxation times for the first saturation level S for a sample fully saturated with oil.

At 224, the NMR surface relaxation times obtained at 222 can be plotted against the different temperatures.

Figure 4:
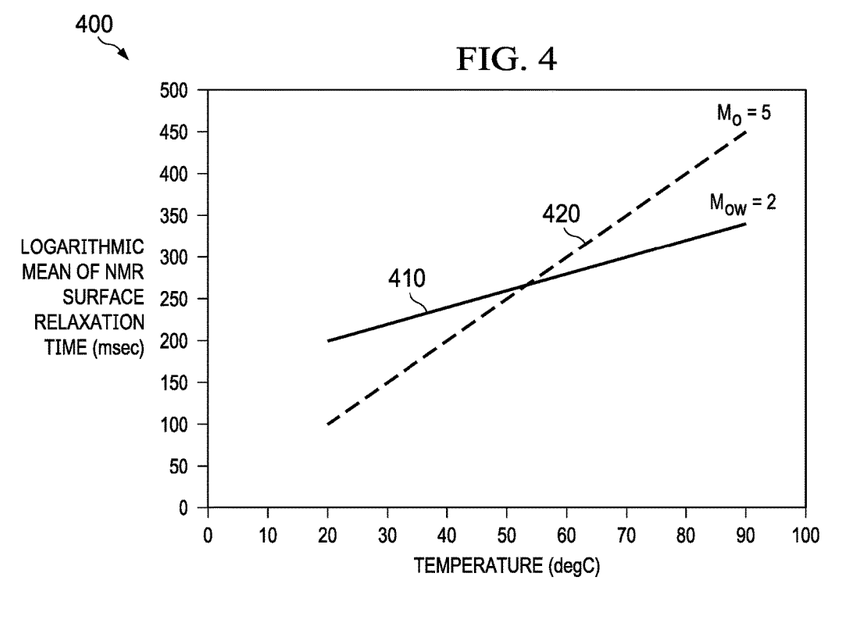
FIG. 4 is a chart illustrating an example comparison of different temperature sensitivities of NMR surface relaxation times, according to an implementation.

At 226, the temperature sensitivity of the NMR surface relaxation times for the sample saturated at a first saturation level and the sample fully saturated with oil can be compared to determine the wettability index. FIG. 4 is a chart 400 illustrating an example comparison of different temperature sensitivities of NMR surface relaxation times, according to an implementation. The data points in the chart 400 is obtained in a lab experiment. The x-axis of the chart 400 represents the temperatures under which each measurement is taken, in units of ° C. The line 410 represents the temperature sensitivity of the NMR surface relaxation time for the sample that is saturated at the saturation level S. The line 410 has a slope $M_{O\_W}=2$, which indicates the temperature sensitivity of the NMR surface relaxation time for the sample at the first saturation level S. The line 420 represents the temperature sensitivity of the NMR surface relaxation time for the sample that is fully saturated with oil. The line 420 has a slope $M_O=5$, which indicates the temperature sensitivity of the NMR surface relaxation time for the sample fully saturated by oil.

Accordingly, the wettability index (WI) can be determined based on the ratio of $M_{O\_W}$ and $M_O$, using the following equation:

$$\text{Wettability Index }(WI) = \frac{m_{o\_w}}{m_o} \quad \text{Eq. (3)}$$

In the illustrated example, the WI for the sample is, thus, 2/5=0.4. The value of the WI indicates the wettability of the porous media sample for the saturation level S. In some operations, the process 200 can be repeated for more than one iterations. At each iteration, a different saturation level S is selected at step 206. Accordingly, WIs for each of these different saturation levels can be determined at the step 226 of the corresponding iteration. WIs for different saturation levels can be used to produce relative permeability curve. The relative permeability curve indicates the petrophysical properties of the rocks in the reservoir where the porous media sample is collected, and can be used to predict the hydrocarbon producibility of the reservoir. Furthermore, these WIs can be used in developing Enhanced Oil Recovery (EOR) and Improved Oil Recovery (IOR) process of the reservoir.

As discussed previously, the NMR surface relaxation times T1 and T2 can, each, produce a temperature sensitivity plot. Thus, the wettability index can be obtained based on the temperature sensitivity for the NMR surface relaxation time T1 or the temperature sensitivity for the NMR surface relaxation times T2, separately. In some cases, these two wettability indices can be consolidated, for example, averaged, to obtain a combined wettability index. Such approach can provide a more robust measurement result.

Figure 5:
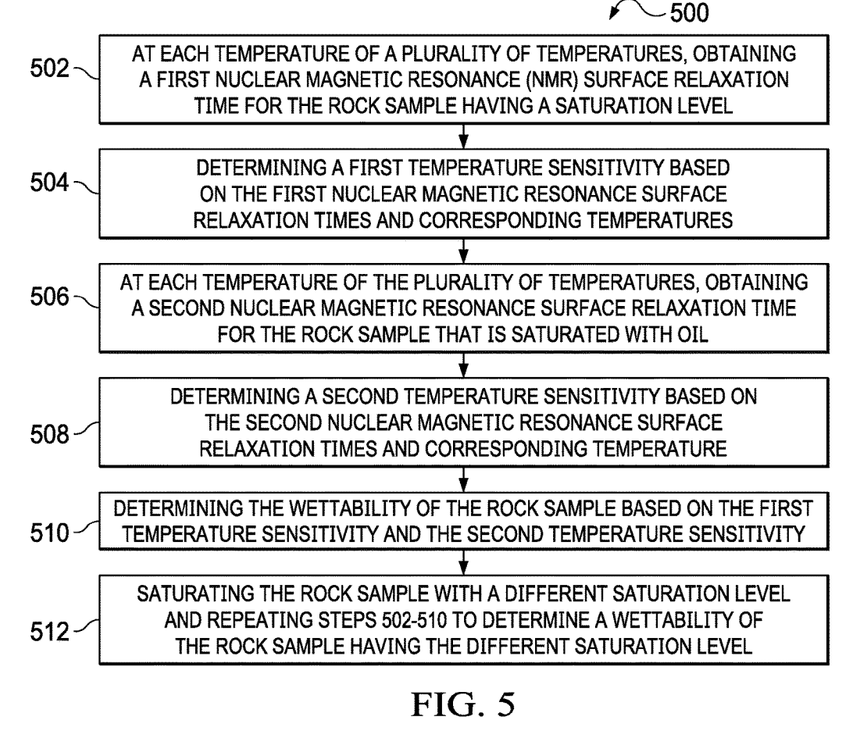
FIG. 5 illustrates an example wettability determination method, according to an implementation.

FIG. 5 illustrates an example wettability determination method 500, according to an implementation. For clarity of presentation, the description that follows generally describes method 500 in the context of FIGS. 1-4 and 6. However, it will be understood that method 500 may be performed, for example, by any other suitable system, environment, software, and hardware, or a combination of systems, environments, software, and hardware, as appropriate. In some cases, the method 500 can be executed on a large scale computer cluster, super computers, or any other computing device or collection of computing devices. In some implementations, various steps of method 500 can be run in parallel, in combination, in loops, or in any order.

At 502, at each temperature of a plurality of temperatures, a first Nuclear Magnetic Resonance (NMR) surface relaxation time for the rock sample having a saturation level is obtained. At 504, a first temperature sensitivity is determined based on the first NMR surface relaxation times and corresponding temperatures. At 506, at each temperature of the plurality of temperatures, a second NMR surface relaxation time for the rock sample that is saturated with oil is obtained. At 508, a second temperature sensitivity is determined based on the second NMR surface relaxation times and corresponding temperature. At 510, the wettability of the rock sample is determined based on the first temperature sensitivity and the second temperature sensitivity. At 512, the rock sample is injected with a different saturation level, and steps 502-510 are repeated to determine a wettability of the rock sample having the different saturation level.

Figure 6:
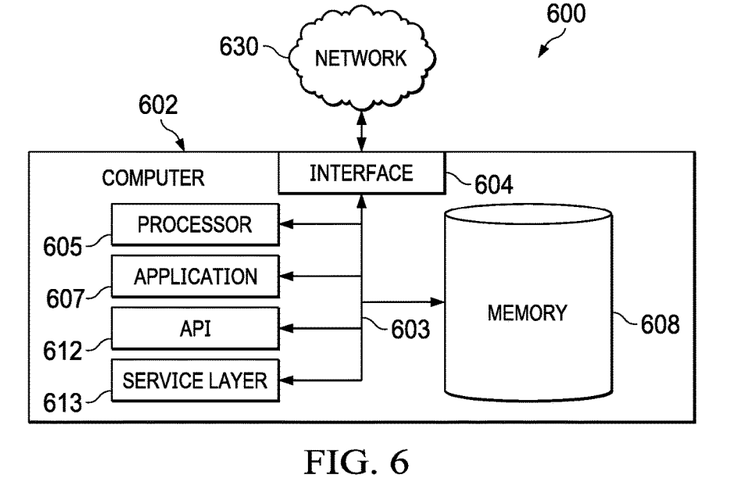
FIG. 6 is a high level architecture block diagram of a wettability analyzing system, according to an implementation.

FIG. 6 is a high level architecture block diagram of a wettability analyzing system 600 that analyzes wettability based on the methods described in this disclosure, according to an implementation. At a high level, the illustrated system 600 includes a computer 602 coupled with a network 630.

The described illustration is only one possible implementation of the described subject matter and is not intended to limit the disclosure to the single described implementation. Those of ordinary skill in the art will appreciate the fact that the described components can be connected, combined, or used in alternative ways, consistent with this disclosure.

The network 630 facilitates communication between the computer 602 and other components, for example, components that obtain observed data for a location and transmit the observed data to the computer 602. The network 630 can be a wireless or a wireline network. The network 630 can also be a memory pipe, a hardware connection, or any internal or external communication paths between the components.

The computer 602 includes a computing system configured to perform the method as described in this disclosure. For example, the computer 602 can be used to implement the NMR controller 102 and the analyzer 120 illustrated in FIG. 1. In some cases, the method can be implemented in an executable computing code, for example, C/C++ executable codes. In some cases, the computer 602 can include a standalone LINUX system that runs batch applications. In some cases, the computer 602 can include mobile or personal computers.

The computer 602 may comprise a computer that includes an input device, such as a keypad, keyboard, touch screen, microphone, speech recognition device, other devices that can accept user information, or an output device that conveys information associated with the operation of the computer 602, including digital data, visual or audio information, or a graphic user interface (GUI).

The computer 602 can serve as a client, network component, a server, a database, or other persistency, or any other component of the system 600. In some implementations, one or more components of the computer 602 may be configured to operate within a cloud-computing-based environment.

At a high level, the computer 602 is an electronic computing device operable to receive, transmit, process, store, or manage data and information associated with the system 600. According to some implementations, the computer 602 may also include, or be communicably coupled with, an application server, e-mail server, web server, caching server, streaming data server, business intelligence (BI) server, or other server.

The computer 602 can receive requests over network 630 from a client application (for example, executing on another computer 602) and respond to the received requests by processing said requests in an appropriate software application. In addition, requests may also be sent to the computer 602 from internal users (for example, from a command console), external or third parties, or other automated applications.

Each of the components of the computer 602 can communicate using a system bus 603. In some implementations, any or all the components of the computer 602, both hardware or software, may interface with each other or the interface 604, over the system bus 603, using an application programming interface (API) 612 or a service layer 613. The API 612 may include specifications for routines, data structures, and object classes. The API 612 may be either computer language-independent or -dependent and refer to a complete interface, a single function, or even a set of APIs. The service layer 613 provides software services to the computer 602 or the system 600. The functionality of the computer 602 may be accessible for all service consumers using this service layer. Software services, such as those provided by the service layer 613, provide reusable, defined business functionalities, through a defined interface. For example, the interface may be software written in JAVA, C++, or suitable language providing data in Extensible Markup Language (XML) format. While illustrated as an integrated component of the computer 602, alternative implementations may illustrate the API 612 or the service layer 613 as stand-alone components in relation to other components of the computer 602 or the system 600. Moreover, any or all parts of the API 612 or the service layer 613 may be implemented as sub-modules of another software module, enterprise application, or hardware module, without departing from the scope of this disclosure.

The computer 602 includes an interface 604. Although illustrated as a single interface 604 in FIG. 6, two or more interfaces 604 may be used according to particular needs, desires, or particular implementations of the computer 602 or system 600. The interface 604 is used by the computer 602 for communicating with other systems in a distributed environment—including within the system 600—connected to the network 630 (whether illustrated or not). Generally, the interface 604 comprises logic encoded in software or hardware in a suitable combination and operable to communicate with the network 630. More specifically, the interface 604 may comprise software supporting one or more communication protocols associated with communications such that the network 630 or interface's hardware is operable to communicate physical signals within and outside of the illustrated system 600.

The computer 602 includes a processor 605. Although illustrated as a single processor 605 in FIG. 6, two or more processors may be used according to particular needs, desires, or particular implementations of the computer 602 or the system 600. Generally, the processor 605 executes instructions and manipulates data to perform the operations of the computer 602. Specifically, the processor 605 executes the functionality required for processing geophysical data.

The computer 602 also includes a memory 608 that holds data for the computer 602 or other components of the system 600. Although illustrated as a single memory 608 in FIG. 6, two or more memories may be used according to particular needs, desires, or particular implementations of the computer 602 or the system 600. While memory 608 is illustrated as an integral component of the computer 602, in alternative implementations, memory 608 can be external to the computer 602 or the system 600.

The application 607 is a software engine providing functionality according to particular needs, desires, or particular implementations of the computer 602 or the system 600, particularly with respect to functionality required for processing geophysical data. For example, application 607 can serve as one or more components or applications described in FIGS. 1-5. Further, although illustrated as a single application 607, the application 607 may be implemented as multiple applications 607, on the computer 602. In addition, although illustrated as integral to the computer 602, in alternative implementations, the application 607 can be external to the computer 602 or the system 600.

There may be any number of computers 602 associated with, or external to, the system 600 and communicating over network 630. Further, the terms "client," "user," and other appropriate terminology may be used interchangeably, as appropriate, without departing from the scope of this disclosure. Moreover, this disclosure contemplates that many users may use one computer 602, or that one user may use multiple computers 602.

Described implementations of the subject matter can include one or more features, alone or in combination.

For example, in a first implementation, a method for measuring wettability of a rock sample includes: at each temperature of a plurality of temperatures, obtaining a first Nuclear Magnetic Resonance (NMR) surface relaxation time for the rock sample having a saturation level; determining a first temperature sensitivity based on the first NMR surface relaxation times and corresponding temperatures; at each temperature of the plurality of temperatures, obtaining a second Nuclear Magnetic Resonance (NMR) surface relaxation time for the rock sample that is saturated with oil; determining a second temperature sensitivity based on the second NMR surface relaxation times and corresponding temperature; and determining the wettability of the rock sample based on the first temperature sensitivity and the second temperature sensitivity.

The foregoing and other implementations can each, optionally, include one or more of the following features, alone or in combination:

A first aspect, combinable with the general implementation, where obtaining the first NMR surface relaxation time comprises: measuring an NMR relaxation time of the oil; measuring an NMR relaxation time of the rock sample having the saturation level; and determining the first NMR surface relaxation time based on the NMR relaxation time of the oil and the NMR relaxation time of the rock sample having the saturation level.

A second aspect, combinable with any of the previous or following aspects, where the first NMR surface relaxation time is determined according to equation:

$$\frac{1}{T_{1,s,Surface}} = \frac{1}{T_{1,S,Apparent}} - \frac{1}{T_{1,O,Bulk}}$$

where $T_{1,s,Surface}$ represents the first NMR surface relaxation time, $T_{1,O,Bulk}$ represents the NMR relaxation time of the oil, and $T_{1,S,Apparent}$ represents the NMR relaxation time of the rock sample having the saturation level.

A third aspect, combinable with any of the previous or following aspects, where the first temperature sensitivity is determined based on a slope of a temperature sensitivity plot obtained based on the first NMR surface relaxation times and the corresponding temperatures.

A fourth aspect, combinable with any of the previous or following aspects, where the temperature sensitivity plot is obtained by converting the first NMR surface relaxation times using a logarithmic scale.

A fifth aspect, combinable with any of the previous or following aspects, where the wettability of the rock sample is determined according to equation:

$$\text{Wettability Index } (WI) = \frac{m_{o\_w}}{m_o}$$

where WI represents the wettability of the rock sample, $m_{o\_w}$ represents the first temperature sensitivity, and $m_o$ represents the second temperature sensitivity.

A sixth aspect, combinable with any of the previous or following aspects, the method further comprising: saturating the rock sample with a different saturation level; and determining a wettability of the rock sample having the different saturation level.

A seventh aspect, combinable with any of the previous or following aspects, where the first NMR surface relaxation time is determined based on at least of one of a T1 relaxation time or a T2 relaxation time.

An eighth aspect, combinable with any of the previous or following aspects, where the first NMR surface relaxation time is determined based on the T1 relaxation time, and the wettability is a first wettability the method further comprising: at each temperature of the plurality of temperatures, obtaining a third NMR surface relaxation time for the rock sample having a saturation level, where the third NMR surface relaxation time is determined based on the T2 relaxation time; determining a third temperature sensitivity based on the third NMR surface relaxation times and corresponding temperatures; at each temperature of the plurality of temperatures, obtaining a fourth Nuclear Magnetic Resonance (NMR) surface relaxation time for the rock sample that is saturated with oil, where the fourth NMR surface relaxation time is determined based on the T2 relaxation time; determining a fourth temperature sensitivity based on the fourth NMR surface relaxation times and corresponding temperature; determining a second wettability of the rock sample based on the third temperature sensitivity and the fourth temperature sensitivity; and determining a combined wettability of the rock sample based on the first wettability and the second wettability.

A ninth aspect, combinable with any of the previous or following aspects, the method further comprising: saturating the rock sample with heavy water ($D_2O$); and after saturating the rock sample with $D_2O$, injecting oil into the rock sample.

A tenth aspect, combinable with any of the previous or following aspects, the method further comprising: after injecting the oil into the rock sample, aging the rock sample prior to measuring an NMR relaxation time of the rock sample.

In a second implementation, a non-transitory computer-readable medium storing instructions which, when executed, cause a computer to perform operations comprising: at each temperature of a plurality of temperatures, obtaining a first Nuclear Magnetic Resonance (NMR) surface relaxation time for a rock sample having a saturation level; determining a first temperature sensitivity based on the first NMR surface relaxation times and corresponding temperatures; at each temperature of the plurality of temperatures, obtaining a second Nuclear Magnetic Resonance (NMR) surface relaxation time for the rock sample that is saturated with oil; determining a second temperature sensitivity based on the second NMR surface relaxation times and corresponding temperature; and determining a wettability of the rock sample based on the first temperature sensitivity and the second temperature sensitivity.

The foregoing and other implementations can each, optionally, include one or more of the following features, alone or in combination:

A first aspect, combinable with the general implementation, where obtaining the first NMR surface relaxation time comprises: measuring an NMR relaxation time of the oil; measuring an NMR relaxation time of the rock sample having the saturation level; and determining the first NMR surface relaxation time based on the NMR relaxation time of the oil and the NMR relaxation time of the rock sample having the saturation level.

A second aspect, combinable with any of the previous or following aspects, where the first NMR surface relaxation time is determined according to equation:

$$\frac{1}{T_{1,s,Surface}} = \frac{1}{T_{1,S,Apparent}} - \frac{1}{T_{1,O,Bulk}}$$

where $T_{1,s,Surface}$ represents the first NMR surface relaxation time, $T_{1,O,Bulk}$ represents the NMR relaxation time of the oil, and $T_{1,S,Apparent}$ represents the NMR relaxation time of the rock sample having the saturation level.

A third aspect, combinable with any of the previous or following aspects, where the first temperature sensitivity is determined based on a slope of a temperature sensitivity plot obtained based on the first NMR surface relaxation times and the corresponding temperatures.

A fourth aspect, combinable with any of the previous or following aspects, where the temperature sensitivity plot is obtained by converting the first NMR surface relaxation times using a logarithmic scale.

A fifth aspect, combinable with any of the previous or following aspects, where the wettability of the rock sample is determined according to equation:

$$\text{Wettability Index } (WI) = \frac{m_{o\_w}}{m_o}$$

where WI represents the wettability of the rock sample, $m_{o\_w}$ represents the first temperature sensitivity, and $m_o$ represents the second temperature sensitivity.

A sixth aspect, combinable with any of the previous or following aspects, where the first NMR surface relaxation time is determined based on at least of one of a T1 relaxation time or a T2 relaxation time.

In a third implementation, a system includes a nuclear magnetic resonance (NMR) instrument configured to, at each temperature of a plurality of temperatures: measure an NMR relaxation time of oil; measure an NMR relaxation time of a rock sample having a saturation level; and measure an NMR relaxation time of the rock sample saturated with oil; a computer system connected to the NMR instrument, where the computer system comprises: at least one hardware processor; and a non-transitory computer-readable storage medium coupled to the at least one hardware processor and storing programming instructions for execution by the at least one hardware processor, where the programming instructions, when executed, cause the at least one hardware processor to perform operations comprising: at each temperature of the plurality of temperatures, determining a first NMR surface relaxation time for the rock sample having a saturation level based on the NMR relaxation time of the oil and the NMR relaxation time of the rock sample having the saturation level; determining a first temperature sensitivity based on the first NMR surface relaxation times and corresponding temperatures; at each temperature of the plurality of temperatures, determining a second NMR surface relaxation time for the rock sample saturated with oil based on the NMR relaxation time of the oil and the NMR relaxation time of the rock sample saturated with oil; determining a second temperature sensitivity based on the second NMR surface relaxation times and corresponding temperatures; and determining a wettability of the rock sample based on the first temperature sensitivity and the second temperature sensitivity.

The foregoing and other implementations can each, optionally, include one or more of the following features, alone or in combination:

A first aspect, combinable with the general implementation, where the wettability of the rock sample is determined according to equation:

$$\text{Wettability Index }(WI) = \frac{m_{o\_w}}{m_o}$$

where WI represents the wettability of the rock sample, $m_{o\_w}$ represents the first temperature sensitivity, and $m_o$ represents the second temperature sensitivity.

Implementations of the subject matter and the functional operations described in this specification can be implemented in digital electronic circuitry, in tangibly embodied computer software or firmware, in computer hardware, including the structures disclosed in this specification and their structural equivalents, or in combinations of one or more of them. Implementations of the subject matter described in this specification can be implemented as one or more computer programs, that is, one or more modules of computer program instructions encoded on a tangible, non-transitory computer-storage medium for execution by, or to control the operation of, data processing apparatus. Alternatively or in addition, the program instructions can be encoded on an artificially generated propagated signal, for example, a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of one or more of them.

The terms "data processing apparatus," "computer," or "electronic computer device" (or equivalent as understood by one of ordinary skill in the art) refer to data processing hardware and encompass all kinds of apparatus, devices, and machines for processing data, including by way of example, a programmable processor, a computer, or multiple processors or computers. The apparatus can also be, or further include, special purpose logic circuitry, for example, a central processing unit (CPU), a FPGA (field programmable gate array), or an ASIC (application-specific integrated circuit). In some implementations, the data processing apparatus or special purpose logic circuitry may be hardware-based or software-based. The apparatus can optionally include code that creates an execution environment for computer programs, for example, code that constitutes processor firmware, a protocol stack, a database management system, an operating system, or a combination of one or more of them. The present disclosure contemplates the use of data processing apparatuses with or without conventional operating systems, for example LINUX, UNIX, WINDOWS, MAC OS, ANDROID, or IOS.

A computer program, which may also be referred to or described as a program, software, a software application, a module, a software module, a script, or code can be written in any form of programming language, including compiled or interpreted languages, or declarative or procedural languages, and it can be deployed in any form, including as a stand-alone program or as a module, component, subroutine, or other unit suitable for use in a computing environment. A computer program may, but need not, correspond to a file in a file system. A program can be stored in a portion of a file that holds other programs or data, for example, one or more scripts stored in a markup language document, in a single file dedicated to the program in question, or in multiple coordinated files, for example, files that store one or more modules, sub-programs, or portions of code. A computer program can be deployed to be executed on one computer or on multiple computers that are located at one site or distributed across multiple sites and interconnected by a communication network. While portions of the programs illustrated in the various figures are shown as individual modules that implement the various features and functionality through various objects, methods, or other processes, the programs may instead include a number of sub-modules, third-party services, components, or libraries. Conversely, the features and functionality of various components can be combined into single components, as appropriate.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, for example, a CPU, an FPGA, or an ASIC.

Computers suitable for the execution of a computer program can be based on general or special purpose microprocessors, both, or any other kind of CPU. Generally, a CPU will receive instructions and data from a read-only memory (ROM) or a random access memory (RAM) or both. The essential elements of a computer are a CPU for performing or executing instructions and one or more memory devices for storing instructions and data. Generally, a computer will also include, or be operatively coupled to, receive data from or transfer data to, or both, one or more mass storage devices for storing data, for example, magnetic, magneto-optical disks, or optical disks. However, a computer need not have such devices. Moreover, a computer can be embedded in another device, for example, a mobile telephone, a personal digital assistant (PDA), a mobile audio or video player, a game console, a global positioning system (GPS) receiver, or a portable storage device, for example, a universal serial bus (USB) flash drive, to name just a few.

Computer-readable media (transitory or non-transitory, as appropriate) suitable for storing computer program instructions and data include all forms of non-volatile memory, media and memory devices, including by way of example semiconductor memory devices, for example, erasable programmable read-only memory (EPROM), electrically erasable programmable read-only memory (EEPROM), and flash memory devices; magnetic disks, for example, internal hard disks or removable disks; magneto-optical disks; and CD-ROM, DVD+/-R, DVD-RAM, and DVD-ROM disks. The memory may store various objects or data, including caches, classes, frameworks, applications, backup data, jobs, web pages, web page templates, database tables, repositories storing business or dynamic information, and any other appropriate information including any parameters, variables, algorithms, instructions, rules, constraints, or references thereto. Additionally, the memory may include any other appropriate data, such as logs, policies, security or access data, or reporting files. The processor and the memory can be supplemented by, or incorporated in, special purpose logic circuitry.

To provide for interaction with a user, implementations of the subject matter described in this specification can be implemented on a computer having a display device, for example, a CRT (cathode ray tube), LCD (liquid crystal display), LED (Light Emitting Diode), or plasma monitor, for displaying information to the user and a keyboard and a pointing device, for example, a mouse, trackball, or trackpad by which the user can provide input to the computer. Input may also be provided to the computer using a touchscreen, such as a tablet computer surface with pressure sensitivity or a multi-touch screen using capacitive or electric sensing. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

The term "graphical user interface," or "GUI," may be used in the singular or the plural to describe one or more graphical user interfaces and each of the displays of a particular graphical user interface. Therefore, a GUI may represent any graphical user interface, including but not limited to, a web browser, a touch screen, or a command line interface (CLI) that processes information and efficiently presents the information results to the user. In general, a GUI may include a plurality of user interface (UI) elements, some or all associated with a web browser, such as interactive fields, pull-down lists, and buttons operable by the business suite user. These UI elements may be related to or represent the functions of the web browser.

Implementations of the subject matter described in this specification can be implemented in a computing system that includes a back-end component, for example, as a data server, or that includes a middleware component, for example, an application server, or that includes a front-end component, for example, a client computer having a graphical user interface or a Web browser through which a user can interact with an implementation of the subject matter described in this specification, or any combination of one or more such back-end, middleware, or front-end components. The components of the system can be interconnected by any form or medium of wireline or wireless digital data communication, for example, a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) using, for example, 802.11 a/b/g/n or 802.20, and all or a portion of the Internet. The network may communicate with, for example, Internet Protocol (IP) packets, Frame Relay frames, Asynchronous Transfer Mode (ATM) cells, voice, video, data, or other suitable information between network addresses.

The computing system can include clients and servers. A client and server are generally remote from each other and typically interact through a communication network. The relationship of client and server arises by virtue of computer programs running on the respective computers and having a client-server relationship to each other.

In some implementations, any or all of the components of the computing system, both hardware or software, may interface with each other or the interface using an application programming interface (API) or a service layer. The API may include specifications for routines, data structures, and object classes. The API may be either computer language independent or dependent and refer to a complete interface, a single function, or even a set of APIs. The service layer provides software services to the computing system. The functionality of the various components of the computing system may be accessible for all service consumers via this service layer. Software services provide reusable, defined business functionalities through a defined interface. For example, the interface may be software written in JAVA, C++, or other suitable language providing data in extensible markup language (XML) format or other suitable format. The API or service layer may be an integral or a stand-alone component in relation to other components of the computing system. Moreover, any or all parts of the service layer may be implemented as child or sub-modules of another software module, enterprise application, or hardware module without departing from the scope of this disclosure.

While this specification contains many specific implementation details, these should not be construed as limitations on the scope of any disclosure or on the scope of what may be claimed, but rather as descriptions of features that may be specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described as acting in certain combinations and even initially claimed as such, one or more features from a claimed combination can in some cases be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking and parallel processing may be advantageous.

Moreover, the separation or integration of various system modules and components in the implementations described previously should not be understood as requiring such separation or integration in all implementations, and it should be understood that the described program components and systems can generally be integrated together in a single software product or packaged into multiple software products.

Accordingly, the previous description of example implementations does not define or constrain this disclosure. Other changes, substitutions, and alterations are also possible without departing from the spirit and scope of this disclosure.

What is claimed is:

1. A method for measuring wettability of a rock sample, comprising:
    saturating the rock sample with heavy water ($D_2O$);
    after saturating the rock sample with $D_2O$, injecting oil into the rock sample;
    at each temperature of a plurality of temperatures, obtaining a first Nuclear Magnetic Resonance (NMR) surface relaxation time for the rock sample having a saturation level;
    determining a first temperature sensitivity based on the first NMR surface relaxation times and corresponding temperatures;
    at each temperature of the plurality of temperatures, obtaining a second Nuclear Magnetic Resonance (NMR) surface relaxation time for the rock sample that is saturated with oil;
    determining a second temperature sensitivity based on the second NMR surface relaxation times and corresponding temperature; and
    determining the wettability of the rock sample based on the first temperature sensitivity and the second temperature sensitivity.

2. The method of claim 1, wherein obtaining the first NMR surface relaxation time comprises:
    measuring a NMR relaxation time of the oil;
    measuring a NMR relaxation time of the rock sample having the saturation level; and
    determining the first NMR surface relaxation time based on the NMR relaxation time of the oil and the NMR relaxation time of the rock sample having the saturation level.

3. The method of claim 2, wherein the first NMR surface relaxation time is determined according to equation:

$$\frac{1}{T_{1,s,Surface}} = \frac{1}{T_{1,S,Apparent}} - \frac{1}{T_{1,O,Bulk}}$$

where $T_{1,s,Surface}$ represents the first NMR surface relaxation time, $T_{1,O,Bulk}$ represents the NMR relaxation time of the oil, and $T_{1,S,Apparent}$ represents the NMR relaxation time of the rock sample having the saturation level.

4. The method of claim 1, wherein the first temperature sensitivity is determined based on a slope of a temperature sensitivity plot obtained based on the first NMR surface relaxation times and the corresponding temperatures.

5. The method of claim 4, wherein the temperature sensitivity plot is obtained by converting the first NMR surface relaxation times using a logarithmic scale.

6. The method of claim 4, wherein the wettability of the rock sample is determined according to equation:

$$\text{Wettability Index } (WI) = \frac{m_{o\_w}}{m_o}$$

where WI represents the wettability of the rock sample, $m_{o\_w}$ represents the first temperature sensitivity, and $m_o$ represents the second temperature sensitivity.

7. The method of claim 1, further comprising:
    saturating the rock sample with a different saturation level; and
    determining a wettability of the rock sample having the different saturation level.

8. The method of claim 1, wherein the first NMR surface relaxation time is determined based on at least of one of a T1 relaxation time or a T2 relaxation time.

9. The method of claim 8, wherein the first NMR surface relaxation time is determined based on the T1 relaxation time, and the wettability is a first wettability the method further comprising:
    at each temperature of the plurality of temperatures, obtaining a third NMR surface relaxation time for the rock sample having a saturation level, wherein the third NMR surface relaxation time is determined based on the T2 relaxation time;
    determining a third temperature sensitivity based on the third NMR surface relaxation times and corresponding temperatures;
    at each temperature of the plurality of temperatures, obtaining a fourth Nuclear Magnetic Resonance (NMR) surface relaxation time for the rock sample that is saturated with oil, wherein the fourth NMR surface relaxation time is determined based on the T2 relaxation time;
    determining a fourth temperature sensitivity based on the fourth NMR surface relaxation times and corresponding temperature;
    determining a second wettability of the rock sample based on the third temperature sensitivity and the fourth temperature sensitivity; and
    determining a combined wettability of the rock sample based on the first wettability and the second wettability.

10. The method of claim 1, further comprising:
    after injecting the oil into the rock sample, aging the rock sample prior to measuring an NMR relaxation time of the rock sample.

11. A method for measuring wettability of a rock sample, comprising:
    at each temperature of a plurality of temperatures, obtaining a first Nuclear Magnetic Resonance (NMR) surface relaxation time for the rock sample having a saturation level, wherein the first NMR surface relaxation time is determined based on a T1 relaxation time;
    determining a first temperature sensitivity based on the first NMR surface relaxation times and corresponding temperatures;

at each temperature of the plurality of temperatures, obtaining a second Nuclear Magnetic Resonance (NMR) surface relaxation time for the rock sample that is saturated with oil;

determining a second temperature sensitivity based on the second NMR surface relaxation times and corresponding temperature;

determining the wettability of the rock sample based on the first temperature sensitivity and the second temperature sensitivity, wherein the wettability is a first wettability;

at each temperature of the plurality of temperatures, obtaining a third NMR surface relaxation time for the rock sample having a saturation level, wherein the third NMR surface relaxation time is determined based on a T2 relaxation time;

determining a third temperature sensitivity based on the third NMR surface relaxation times and corresponding temperatures;

at each temperature of the plurality of temperatures, obtaining a fourth Nuclear Magnetic Resonance (NMR) surface relaxation time for the rock sample that is saturated with oil, wherein the fourth NMR surface relaxation time is determined based on the T2 relaxation time;

determining a fourth temperature sensitivity based on the fourth NMR surface relaxation times and corresponding temperature;

determining a second wettability of the rock sample based on the third temperature sensitivity and the fourth temperature sensitivity; and determining a combined wettability of the rock sample based on the first wettability and the second wettability.

12. The method of claim 11, wherein obtaining the first NMR surface relaxation time comprises:
measuring a NMR relaxation time of the oil;
measuring a NMR relaxation time of the rock sample having the saturation level; and
determining the first NMR surface relaxation time based on the NMR relaxation time of the oil and the NMR relaxation time of the rock sample having the saturation level.

13. The method of claim 12, wherein the first NMR surface relaxation time is determined according to equation:

$$\frac{1}{T_{1,s,Surface}} = \frac{1}{T_{1,S,Apparent}} - \frac{1}{T_{1,O,Bulk}}$$

where $T_{1,s,Surface}$ represents the first NMR surface relaxation time, $T_{1,O,Bulk}$ represents the NMR relaxation time of the oil, and $T_{1,S,Apparent}$ represents the NMR relaxation time of the rock sample having the saturation level.

14. The method of claim 11, wherein the first temperature sensitivity is determined based on a slope of a temperature sensitivity plot obtained based on the first NMR surface relaxation times and the corresponding temperatures.

15. The method of claim 14, wherein the temperature sensitivity plot is obtained by converting the first NMR surface relaxation times using a logarithmic scale.

16. The method of claim 14, wherein the wettability of the rock sample is determined according to equation:

$$\text{Wettability Index } (WI) = \frac{m_{o\_w}}{m_o}$$

where WI represents the wettability of the rock sample, $m_{o\_w}$ represents the first temperature sensitivity, and $m_o$ represents the second temperature sensitivity.

17. The method of claim 11, further comprising:
saturating the rock sample with a different saturation level; and
determining a wettability of the rock sample having the different saturation level.

18. The method of claim 11, further comprising:
saturating the rock sample with heavy water ($D_2O$); and
after saturating the rock sample with $D_2O$, injecting oil into the rock sample.

19. The method of claim 18, further comprising:
after injecting the oil into the rock sample, aging the rock sample prior to measuring an NMR relaxation time of the rock sample.

* * * * *